United States Patent [19]

Delaage

[11] 4,331,646

[45] May 25, 1982

[54] IODINE COMPOUND FOR USE AS A TRACER IN RADIOIMMUNOLOGY

[75] Inventor: Michel Delaage, Marseilles, France

[73] Assignee: Commissariat a l'Energie Atomique, Paris, France

[21] Appl. No.: 50,060

[22] Filed: Jun. 19, 1979

[30] Foreign Application Priority Data

Jun. 20, 1978 [FR] France .............................. 78 18404

[51] Int. Cl.³ ..................... A61K 43/00; G01N 33/56; G01N 33/60; C07C 103/52
[52] U.S. Cl. ............................... 424/1; 260/112.5 R; 260/239.5; 424/179; 424/238
[58] Field of Search ..................... 260/112.5 R, 239.5; 424/1, 12, 179, 238

[56] References Cited

U.S. PATENT DOCUMENTS

| | | | |
|---|---|---|---|
| 4,197,286 | 4/1980 | Rao | 424/12 |
| 4,202,874 | 5/1980 | Akerkar et al. | 23/230 B |
| 4,207,308 | 6/1980 | Spenny | 424/1 |
| 4,209,614 | 6/1980 | Bernstein et al. | 424/12 |

OTHER PUBLICATIONS

Radioimmunoassay of Biologically Active Compounds, Parker, Prentice-Hall, Inc., N.J., 1976, pp. 93-94.

Ohki et al., Prostaglandins, vol. 6, No. 2, Apr. 1974, pp. 137-148.

Primary Examiner—Christine M. Nucker

[57] ABSTRACT

The compound is constituted by a conjugate compound of an antigen having a free carboxylic function and a dipeptide. The dipeptide is constituted by a product of condensation between tyrosine and a peptide, the tyrosine group of the dipeptide being labeled with radioactive iodine.

The compound is highly soluble in water and permits of good recognition by the antibody in antigen-antibody reactions.

10 Claims, 4 Drawing Figures

IODINE COMPOUND FOR USE AS A TRACER IN RADIOIMMUNOLOGY

This invention relates to an iodine compound which can be employed as a tracer in radioimmunology and to a method of preparation of said iodine compound. The iodine compound in accordance with the invention can be employed as a labeled antigen in radioimmunology.

It is recalled that most antigens give rise to specific antigen antibodies and combine with said antibodies to form a complex; the same applies to some of their analogs in which the active antigenic sites are present in their entirety. The antigen-antibody reaction is employed for determining the quantity of antigen in a given medium; this quantitative measurement, first of all of the antigen-antibody reaction, in order to deduce the quantity of antigen in a given medium, can be carried out especially by the method of radioimmunology which involves the use of a tracer. In more exact terms, the radioimmunological method consists in studying the antigen-antibody reaction in the presence of a tracer obtained by labeling the antigen or the antibody or one of their analogs with a radioactive substance such as iodine-125, for example. Among the possible modes of operation, there can be mentioned in particular the method known as competition with excess antigen with respect to the antibody; in this case, the labeled antigen and the unlabeled antigen then compete with each other so as to combine with the antibody in a limited quantity with respect to the total quantity of antigen. The labeled antigen and the antibody are added in known quantity in different measuring tubes; increasing known quantities of unlabeled antigen are added in the tube, thus making it possible to plot a calibration curve: in fact, the free antigen may be separated at any moment from the antigen which is linked with the antibody and the distribution of radioactivity between the free antigen and the bonded complex is measured in the case of each tube.

It is therefore apparent that, when employing the method of radioimmunology, the nature and properties of the labeled antigen are of great importance. This antigen which is preferably labeled with radioactive iodine is prepared either by synthesis of the antigen followed by iodination of the antigen thus prepared or by iodination of the antigen extracted from a human or animal organ, or by preparation of an iodine compound of a type similar to the antigen which naturally exists in the medium to be analyzed.

It is not always possible to carry out direct iodine labeling of the antigen and it may prove necessary to carry out preliminary modification of said antigen prior to introduction of the iodine.

Many preparations of different labeled antigens which entail modification prior to introduction of the iodine have already been studied and developed. The labeled antigens which are particularly worthy of note are those obtained by attachment of tyrosine-methylester to an antigen and labeling with radioactive iodine; this compound has a disadvantage in that it is sparingly soluble in water. Mention can also be made of the labeled antigens obtained by attachment of a reagent known by the name of "Bolton-Hunter", this reagent being constituted by a succinimide ester of hydroxyphenylpropionic acid corresponding to the formula:

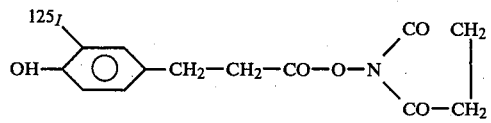

and which is capable of attachment to an antigen; this compound also has the disadvantage of being sparingly soluble in water as well as having an affinity for albumins, with the result that irregularities are liable to arise from the use of the method of radioimmunology.

The invention is precisely directed to an iodine compound which can be employed as a tracer in radioimmunology without being subject to the disadvantages of the compounds recalled in the foregoing. In particular, the compound of the invention has an advantage in that it is highly soluble in water and permits of good recognition by the antibody at the time of analysis by radioimmunology. In other words, said compound ensures that the labeled antigen - antibody reaction is as close as possible to the unlabeled antigen - antibody reaction.

The compound according to the invention is essentially constituted by a conjugate compound of an antigen having a free carboxylic function and a dipeptide, said dipeptide being constituted by a product of condensation between tyrosine and a peptide, the tyrosine group of said dipeptide being labeled with radioactive iodine.

According to the invention, the dipeptide is constituted by a product of condensation of tyrosine with a peptide selected from the group comprising glycine, leucine, isoleucine, alanine, serine, tyrosine, phenylalanine, threonine, valine, histidine, proline; it can also be a product of condensation of tyrosine with lysine, arginine, aspartic acid, glutamic acid, aspartamine, glutamine.

Preferably, glycine is used as the peptide which is to be associated with tyrosine in the dipeptide, thereby producing glycyl-tyrosine having the formula:

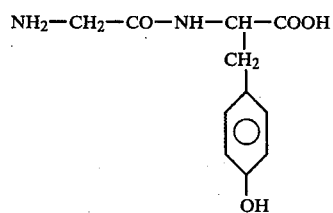

The antigen which is combined with the dipeptide to form the tracer compound of the invention can be a lipophilic hormone such as the juvenile hormone, a prostaglandin such as $PGE_2$, a neurotransmitter such as serotonin.

Similarly, the antigen combined with the dipeptide to form the tracer compound of the invention can be constituted by abscissic acid (vegetable hormone) or by a progesterone.

Thus, with glycyl-tyrosine attached to the juvenile hormone and the tyrosine group being iodinated, the result obtained is a compound having the formula:

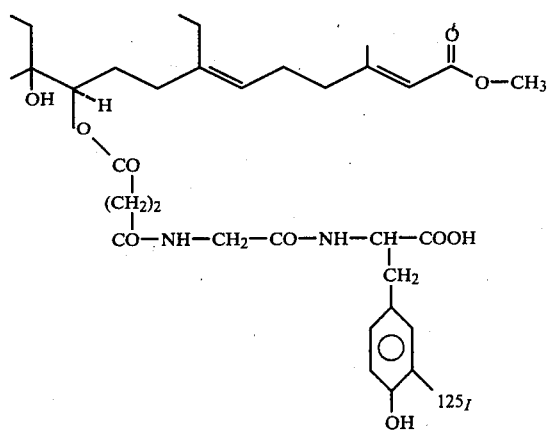

With glycyl-tyrosine attached to the prostaglandin PGE₂ and the tyrosin group being iodinated, the result obtained is a compound having the formula:

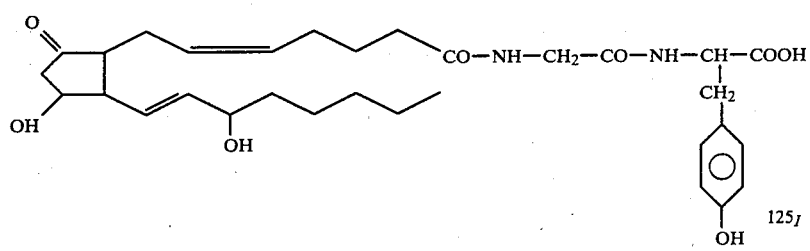

In order to obtain an analog iodinated derivative of serotonin, the glycyl-tyrosine is attached to the 5-hydroxyindole acetic acid, the tyrosine group being iodinated, the result obtained being a tracer compound having the formula:

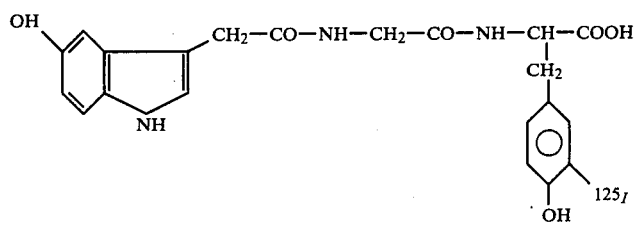

The invention is also directed to a method of preparation of the iodine compounds mentioned above. This method essentially comprises a reaction involving condensation of an antigen with a dipeptide, said dipeptide being constituted by a product of condensation between the tyrosine and a peptide, and a reaction involving iodination of the tyrosine group.

In a preferred embodiment of the invention, the antigen is previously activated by ethyl chloroformate.

According to the invention, it is possible either to carry out in a first step the condensation reaction between the antigen and the dipeptide and, in a second step, to carry out the tyrosine group iodination reaction or to carry out in a first step iodination of the tyrosine group of the dipeptide and then, in a second step, condensation of the dipeptide which has thus been labeled by the antigen. The mode of execution of the method just mentioned is employed only in the event that the antigen alone does not withstand iodination.

According to the invention, the iodination reaction is a reaction of conventional type which consists in employing iodine-125 in the form of sodium iodide and chloramine T, in stopping the oxidation-reduction reaction which results in the formation of iodine-125 and attachment of said iodine-125 to the tyrosine group of the dipeptide by means of sodium metabisulphite. The iodine compounds obtained are then purified by chromatography on Sephadex G 25 gel.

The tyrosine-peptide dipeptide is prepared beforehand by any known method which permits bonding between two peptides, for example by making use of carbodiimide.

A more complete understanding of the invention will be gained from a perusal of the following description which gives examples of preparation of iodine compounds, reference being made to the accompanying drawings in which.

Figure 1:
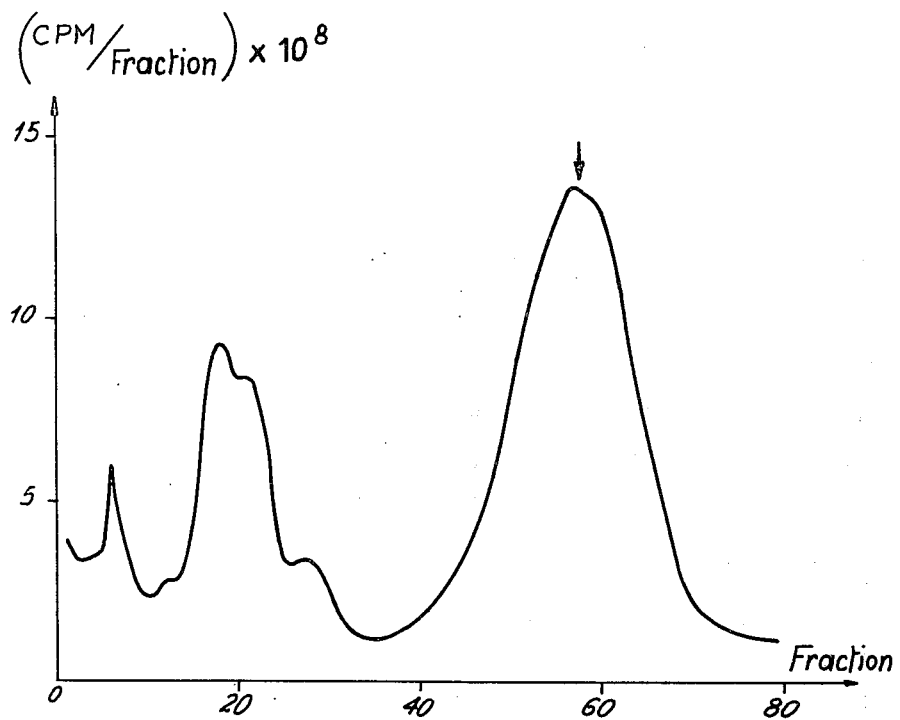
FIG. 1 illustrates the chromatogram obtained at the time of purification, in a Sephadex G 25 column, of the compound obtained in Example 3 and consisting of glycyl L-tyrosine combined with succinyl serotonin.

Among these examples, only Examples 1, 2, 3 and 5 relate to the preparation of iodine compounds in accordance with the invention whilst Examples 4 and 6 are given solely by way of comparison.

EXAMPLE 1

It is endeavored to prepare an iodine compound consisting of glycyl - iodinated tyrosine dipeptide attached to the prostaglandin PGE$_2$, the operation being performed at 4° C.

2 mg of prostaglandin PGE$_2$ are dissolved in 200 μl of dimethylformamide with 20 μl of a solution obtained from 100 μl of triethylamine and 1 ml of dimethylformamide.

At the starting point or "zero instant", there are added to this solution 10 μl of a solution obtained from 50 μl of ethylchloroformate and 750 μl of dimethylformamide.

When 10 minutes have elapsed, there are added 100 μl of a solution obtained from 16 mg of glycyltyrosine dipeptide, 500 μl of dimethylformamide and 100 μl of a solution obtained from 100 μl of triethylamine and 1 ml of water.

When 15 minutes have elapsed, there are added 500 μl of a 0.1 M neutral buffer solution of citrate having a pH of 6.2 in order to stop the reaction.

The final solution thus obtained is introduced into a chromatographic column containing Sephadex gel equilibrated in a NaCl solution having a concentration of $2 \times 10^{-2}$ M.

Elution is carried out with a gradient of $2 \times 800$ ml of $2 \times 10^{-2}$ M NaCl and 0.4 M NaCl.

The conjugate compound prostaglandin PGE$_2$-glycyltyrosine is recovered at the outlet of the column and leaves this latter slightly before the mid-point of the elution gradient. The different fractions of PGE$_2$-glycyltyrosine are collected, the concentration is measured on the basis of the optical density at 280 nm and is adjusted to approximately $1.5 \times 10^{-4}$ M.

Iodination of the conjugate compound PGE$_2$-glycyltyrosine (1 microgram) is then carried out by adding a solution of chloramine T (10 micrograms) and 1 to 2 millicuries of sodium iodide which is followed at the end of a predetermined time interval by the addition of sodium metabisulphite.

EXAMPLE 2

It is endeavored to prepare an iodine compound which is analogous to serotonin and consists of glycyl-tyrosine combined with 5-hydroxy-indole acetic acid labeled with iodine-125, the operation being performed at 4° C.

2 mg of 5-hydroxy-indole-acetic acid are dissolved with 200 μl of dimethylformamide and 20 μl of a solution prepared from 100 μl of triethylamine and 1 ml of dimethylformamide.

At the zero instant, there are added 10 μl of a solution prepared from 50 μl of ethylchloroformate and 750 ml of dimethylformamide, thereby obtaining a solution A.

When 10 minutes have elapsed, iodination of the glycyl-tyrosine dipeptide is carried out separately in another tube. Thus a solution is prepared by mixing 2 mg of glycyl-tyrosine and 2 ml of water; and there is added to 25 μl of said solution 1 ml of a 0.1 M buffer solution of phosphate having a pH of 7.5. To 30 μl of the solution thus obtained are added 5 μl of a sodium metabisulphite solution having a concentration of 0.6 mg/ml in a 0.1 M buffer solution of phosphate having a pH of 7.5, 20 μl of a 100 mCi/ml solution of $^{125}$INa, then 20 times 1 μl of a 1 mg/ml solution of chloramine T during a total time interval of 1 minute. There are then added 50 μl of a 0.6 mg/ml sodium metasulphite solution in a 0.1 M buffer solution of phosphate having a pH in the vicinity of 7.5 and 10 μl of a solution prepared from 100 μl of triethylamine and 1 ml of dimethylformamide; a solution B is thus obtained.

After 15 minutes have elapsed, there are added 10 μl of a solution prepared from 10 μl of butylamine and 1 ml of dimethylformamide in the solution A which constitutes the activation reaction medium of the 5-hydroxyindole acetic acid.

After 16 minutes have elapsed, the 240 μl of solution A which has received an addition of butylamine and dimethylformamide as before are added to the 135 μl of solution B which constitutes the iodination mixture.

After 21 minutes have elapsed, 500 μl of a 0.1 M buffer solution of citrate having a pH in the vicinity of 6.2 are added to the solution thus obtained.

The final solution obtained is introduced into a chromatographic column of Sephadex G 25 gel equilibrated in the 0.1 M buffer solution of citrate having a pH in the vicinity of 6.2. The conjugate iodine compound of 5-hydroxy-indole acetic acid and glycyl-tyrosine is eluted with a volume which is three times greater than the volume required for elution of the iodide.

EXAMPLE 3

This example relates to the preparation of an iodine compound consisting of glycyl-tyrosine combined with succinyl-serotonin.

First of all, the succinyl derivative of serotonin is prepared as follows.

There are mixed together 40 mg of serotonin, 90 mg of succinic anhydride, 2 ml of water and 163 μl of 9 M KOH. The mixture is stirred for approximately 5 minutes in order to obtain the reaction, whereupon said mixture is purified in a column of Sephadex G 25 (2.5×80 cm), elution being performed by means of distilled water. The fraction containing the succinyl compound is collected and lyophilized.

The iodine compound is then prepared as follows, the operation being performed at 4° C.

3 mg of the succinyl derivative of serotonin are dissolved with 200 μl of dimethylformamide and 20 μl of a solution prepared from 100 μl of triethylamine and 1 ml of dimethylformamide.

At the zero instant, there are added 10 μl of a solution prepared from 50 μl of ethylchloroformate and 750 ml of dimethylformamide, thus obtaining a solution A.

When 10 minutes have elapsed, iodination of the glycyl-tyrosine dipeptide is carried out separately in another tube: a solution is prepared by mixing 2 mg of glycyl-tyrosine and 2 ml of water; and there is added to 25 μl of said solution 1 ml of a 0.1 M buffer solution of phosphate having a pH of 7.5. To 30 μl of the solution thus obtained are added 5 μl of a sodium metabisulphite solution having a concentration of 0.6 mg/ml in a 0.1 M buffer solution of phosphate having a pH of 7.5, 20 μl of a 100 mCi/ml solution of $^{125}$INa, then 20 times 1 μl of a 1 mg/ml solution of chloramine T during a total time interval of 1 minute. There are then added 50 μl of a 0.6 mg/ml sodium metabisulphite solution in a 0.1 M phosphate buffer solution having a pH in the vicinity of 7.5 and 10 μl of a solution prepared from 100 μl of triethylamine and 1 ml of dimethylformamide; a solution B is thus obtained.

When 15 minutes have elapsed, there are added 10 μl of a solution prepared from 10 μl of butylamine and 1 ml of dimethylformamide in the solution A which constitutes the activation reaction medium of the succinyl derivative of serotonin.

When 16 minutes have elapsed, the 240 µl of solution A which has received an addition of butylamine and dimethylformamide as before is added to the 135 µl of solution B which constitutes the iodination mixture.

When 21 minutes have elapsed, 500 µl of a 0.1 M buffer solution of citrate having a pH in the vicinity of 6.2 are added to the solution thus obtained.

The final solution obtained is introduced into a chromatographic column of Sephadex G 25 gel (0.9×58 cm) equilibrated in the 0.1 M citrate buffer solution having a pH in the vicinity of 6.2 and elution is carried out by means of the same citrate buffer solution by collecting the eluted solution in fractions of 2.85 ml.

The results obtained are given in FIG. 1 which is a chromatogram representing the progressive variation of radioactivity in the fractions which are collected successively.

In this figure, it is apparent that the iodine compound corresponding to the third peak is eluted very rapidly since it appears near the sixtieth fraction.

Moreover, the iodine compound thus obtained is tested against an immune serum diluted between $10^3$ and $10^4$ and a specific degree of fixation is obtained; this compound can be displaced by unlabeled serotonin.

EXAMPLE 4

This example relates to the preparation of an iodine compound obtained by reaction of serotonin with the Bolton-Hunter reagent.

It is recalled that this reagent is marketed by New England Nuclear under reference NEX 120 and consists of a solution in benzene of the succinimide ester of p-hydroxy-phenylpropionic acid, said ester being labeled with radioactive iodine-125.

In order to obtain the iodine compound of serotonin, 25 µl of the Bolton-Hunter reagent is reacted with agitation with 10 µl of a borate buffer solution containing 2 µg of serotonin.

The product obtained is purified by chromatography in a column of Sephadex G 25 (0.9×57.5 cm) equilibrated by a 0.1 M citrate buffer solution having a pH of 6.2 by eluting with said citrate buffer solution and collecting the eluted solution in fractions of 2.9 ml at the beginning of elution, then in fractions of 5.2 ml starting from the thirtieth fraction collected. The total duration of elution is 70 hours.

Figure 2:
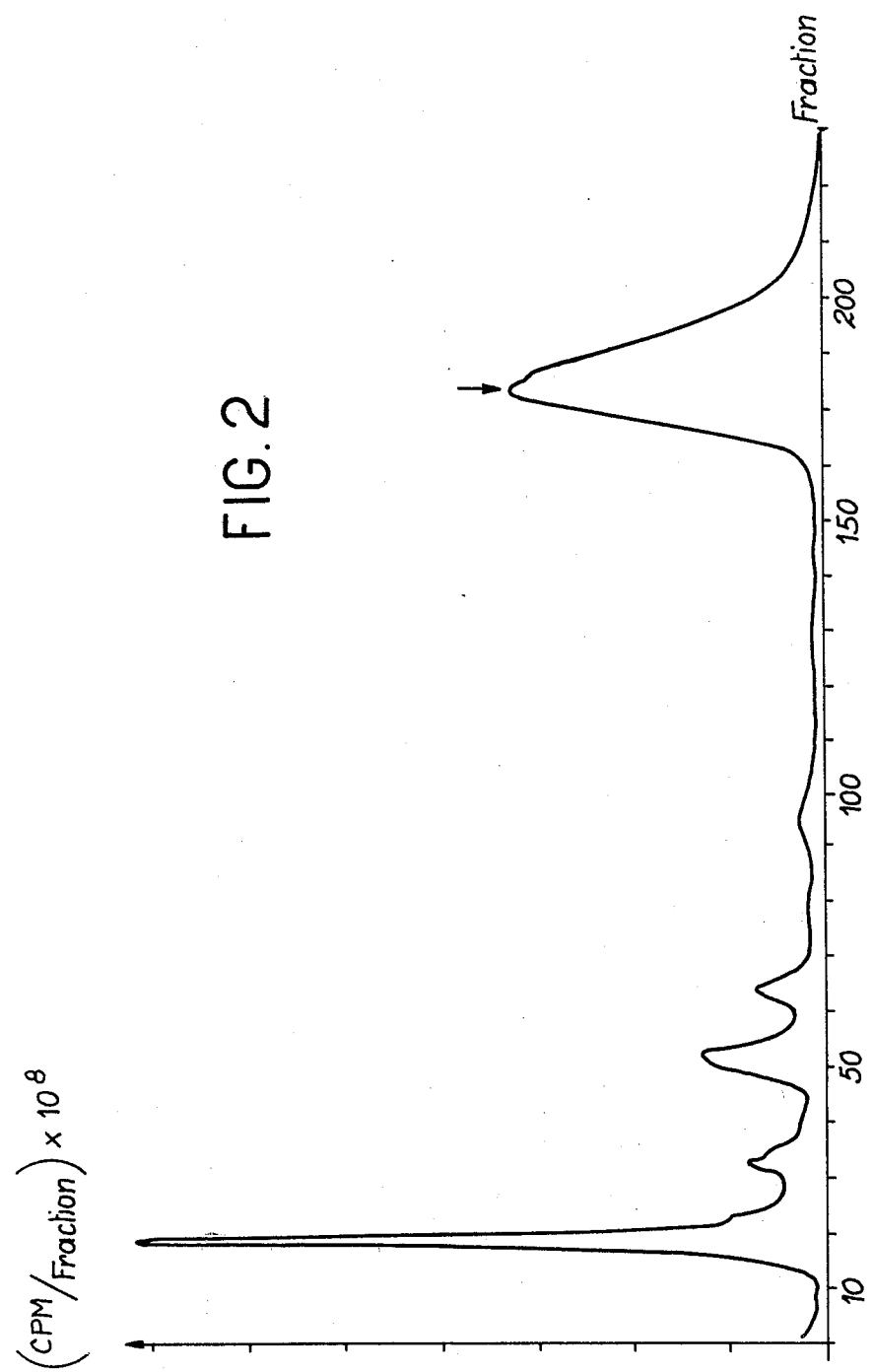
FIG. 2 illustrates the chromatogram obtained by purification, in a column of Sephadex G 25, of the compound obtained in Example 4 or in other words an iodine compound consisting of serotonin labeled with reagent iodine by reaction with the Bolton-Hunter reagent.

The results obtained are given in FIG. 2 which represents the progressive variation of radioactivity in the fractions which are collected successively.

From this figure, it is apparent that the chromatogram exhibits a plurality of peaks and that the highest of these peaks corresponding to the product of coupling of serotonin and of the Bolton-Hunter reagent appears from the 160th fraction collected.

It is thus found that this iodine compound is delivered at a very late stage, namely after approximately three days of elution.

Moreover, by testing this iodine compound against an immune serum diluted 60 times in dialysis at equilibrium, a degree of fixation of the order of 50% is obtained.

However, this fixation is not displaceable by the unlabeled serotonin. It consequently appears that said fixation is primarily due to the albumin and not to the antibodies.

It is thus found that the Bolton-Hunter reagent endows the small molecules with an affinity for albumin, thus constituting a major obstacle for the use of the iodine compound obtained from this reagent in radioimmunology.

EXAMPLE 5

This example relates to the preparation of an iodine compound constituted by glycyl-L-tyrosine combined with the succinyl derivative of the juvenile hormone.

In a first step, the succinyl derivative of the juvenile hormone is prepared in the following manner.

10 µl of juvenile hormone which is present in the form of an oily liquid is dissolved in 1 ml of dioxan; 40 µl of 0.5 N sulphuric acid are then added and the mixture is allowed to stand overnight at 37° C.

Neutralization with sodium hydroxide is then performed and the product obtained is lyophilized.

The lyophilized product is dissolved in 3 ml of dioxan, 100 mg of succinic anhydride and 500 µl of triethylamine are added to the solution; the mixture is then allowed to stand for 24 hours at 37° C. The medium is dried, then lyophilized and the lyophilized product is re-treated in 5 ml of water. The pH is adjusted to a value of 6 and purification is carried out in a Sephadex QAE-A 25 chromatographic ion-exchange column.

The compound is eluted with a sodium chloride solution whose concentration increases as the elution proceeds.

The solution containing the succinyl derivative of the juvenile hormone is then desalted by passing through a chromatographic column which is identical with the column previously employed, elution being performed in this case by means of $10^{-2}$ M hydrochloric acid. The eluted solution is then neutralized and finally lyophilized.

In a second step, the iodine compound consisting of glycyl L-tyrosine combined with the succinyl derivative of the juvenile hormone thus obtained is prepared in the following manner, the operation being carried at 4° C.

2 mg of the succinyl derivative of the juvenile hormone previously obtained are dissolved in 200 µl of dimethylformamide with 20 µl of a solution obtained from 100 µl of triethylamine and 1 ml of dimethylformamide.

At the zero instant, there are added to this solution 10 µl of a solution obtained from 50 µl of ethylchloroformate and 750 µl of dimethylformamide.

When 10 minutes have elapsed, there are added 100 µl of a solution obtained from 16 mg of glycyl-tyrosine dipeptide, 500 µl of dimethylformamide and 100 µl of a solution obtained from 100 µl of triethylamine and 1 ml of water.

When 15 minutes have elapsed, 500 µl of a 0.1 M neutral buffer solution of citrate having a pH of 6.2 are added in order to stop the reaction.

The final solution obtained is introduced into a chromatographic column containing Sephadex gel equilibrated in a NaCl solution having a concentration of $2 \times 10^{-2}$ M.

Elution is carried out with a gradient of $2 \times 800$ ml of $2 \times 10^{-2}$ M NaCl and 0.4 M NaCl.

The conjugate compound consisting of succinyl, juvenile hormone, glycyl-tyrosine, is recovered at the exit of the column and leaves this latter slightly before the mid-point of the elution gradient. The different fractions of succinyl, juvenile hormone, glycyl-tyrosine are then collected. The concentration is measured on the basis of the optical density at 280 nm and adjusted to approximately $1.5 \times 10^{-4}$ M.

Iodination of the conjugate compound consisting of the succinyl derivative of juvenile hormone - glycyl-L-tyrosine (1 microgram) is then carried out by adding a solution of chloramine T (10 micrograms) and from 1 to 2 millicuries of sodium iodide, then by adding sodium metabisulphite after a predetermined period of time has elapsed.

The iodine compound thus obtained is then purified by chromatography in a column of Sephadex G 25 (1.5×95 cm). For this chromatographic operation, elution is carried out by means of a 0.1 M citrate buffer solution having a pH of approximately 6.2 and the eluted solution is collected in fractions of 3.85 ml.

Figure 3:
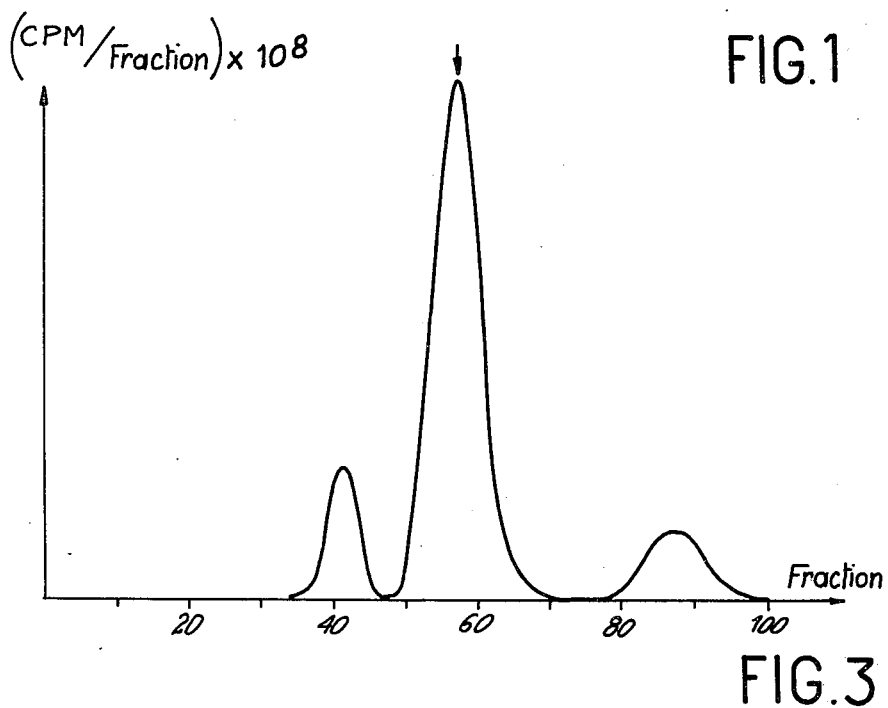
FIG. 3 illustrates the chromatogram obtained by purification, in a column of Sephadex G 25, of the iodine compound obtained in Example 5 consisting of glycyl-L-tyrosine combined with a succinyl derivative of the juvenile hormone.

The results obtained are given in FIG. 3 which is a chromatogram representing the progressive variation of radioactivity in the collected fractions.

From this figure, it is observed that the iodine compound obtained by coupling of the succinyl derivative of the juvenile hormone with glycyl-L-tyrosine is eluted at a very high speed.

Moreover, this compound is highly immunoreactive. In fact, a 50% fixation is obtained with immune serums having a dilution ratio which is higher than $10^6$.

Finally, it is noted that this iodine compound can be handled without any difficulty within plastic tubes and pipets.

EXAMPLE 6

This example relates to the preparation of an iodine compound obtained by coupling of tyrosine-methylester with the succinyl derivative of the juvenile hormone obtained during the first step of Example 5. For this preparation, the operation is performed at 4° C.

2 mg of the succinyl derivative of the juvenile hormone are dissolved in 200 μl of dimethylformamide with 20 μl of a solution obtained from 100 μl of triethylamine and 1 ml of dimethylformamide.

When 10 minutes have elapsed, there are added 100 μl of a solution obtained from 16 mg of tyrosine-methylester, 500 μl of dimethylformamide and 100 μl of a solution obtained from 100 μl of triethylamine and 1 ml of water.

When 15 minutes have elapsed, 500 μl of a 0.1 M neutral buffer solution of citrate having a pH of 6.2 are added in order to stop the reaction.

The final solution obtained is introduced into a chromatographic column containing Sephadex gel equilibrated in a NaCl solution having a concentration of $2 \times 10^{-2}$ M.

Elution is carried out with a gradient of $2 \times 800$ ml of $2 \times 10^{-2}$ M NaCl and 0.4 M NaCl.

The conjugate compound consisting of succinyl derivative of juvenile hormone-tyrosine-methyl ester which leaves the column shortly before the mid-point of the elution gradient is recovered at the exit of the column. The different fractions of succinyl derivative of juvenile hormone-tyrosine-methyl ester are collected, the concentration is measured on the basis of the optical density at 280 nm and adjusted to approximately $1.5 \times 10^{-4}$ M.

Iodination of the conjugate compound consisting of succinyl derivative of juvenile hormone-tyrosine-methyl ester (1 microgram) is then carried out by adding a solution of chloramine T (10 micrograms) and from 1 to 2 millicuries of sodium iodide, then by adding sodium metabisulphite after a predetermined period of time has elapsed.

After iodination, the iodine compound obtained by chromatography in a column of Sephadex G 25 (1.5×90 cm) is purified by carrying out elution by means of a 0.1 M citrate buffer solution having a pH of approximately 6.2 and by collecting the eluted solution in fractions of 4.5 ml.

Figure 4:
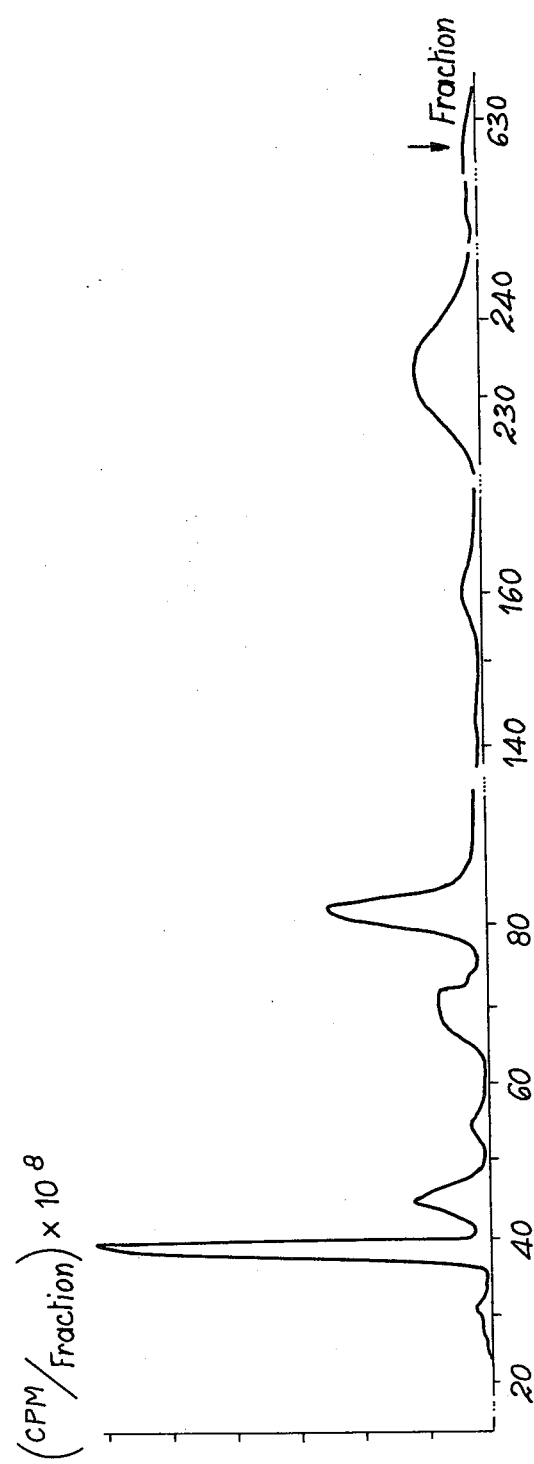
FIG. 4 illustrates the chromatogram obtained by purification, in a column of Sephadex G 25, of the compound obtained in Example 6 or in other words an iodine compound obtained by reaction of the succinyl derivative of the juvenile hormone with tyrosine-methyl ester.

The results obtained are given in FIG. 4 which is a chromatogram representing the progressive variation of radioactivity in the successively eluted fractions.

From this figure, it is observed that the iodine compound obtained by coupling of the tyrosine methyl ester with the succinyl derivative of the juvenile hormone does not readily leave the Sephadex column. In fact, the immunoreactive fraction corresponding to this compound appears only after one week of elution in fractions numbering from 559 to 625.

In contrast to the iodine compound obtained in Example 4, this iodine derivative does not have any affinity for albumin. However, said iodine compound is highly hydrophobic and adheres to all materials, especially plastics. In consequence, the use of this compound from a quantitative standpoint is practically excluded.

Finally, this compound makes it possible to obtain a 50% fixation with an immune serum having a dilution ratio of $10^4$.

It is thus found that the compound of the invention as obtained in Example 5 offers many advantages over the compound obtained in this example. In fact the compound of Example 5 is purified in a very short time, does not adhere to plastic tubes and pipets and makes it possible to obtain a substantial gain in sensitivity and a saving of antibodies by a factor of 100.

As can readily be understood, the examples given in the foregoing do not imply any limitation so far as the present invention is concerned. Iodine compounds according to the invention could be prepared in the same manner by making use of dipeptides other than glycyl-tyrosine. Examples of these are compounds of tyrosine with peptides such as leucine, isoleucine, alanine, serine, tyrosine, phenylalanine, threonine, valine, histidine, proline, lysine, arginine, aspartic acid, glutamic acid, aspartamine, glutamine.

The iodine compounds according to the invention have an advantage in that the presence of the dipeptide does not basically alter the character of the antigen and makes it possible to employ all the methods of separation applicable to small molecules (adsorption on charcoal, dialysis and the like) at the time of the subsequent separations during the method of radioimmunology. Moreover, the fact that the tyrosine group is placed in the end position C ensures that, during the method of radioimmunology, maximum separation is achieved between the antibody and the iodinated tyrosine portion since the volume of this latter could otherwise hinder the linkage between labeled antigen and antibody. Moreover, the compounds of the invention are highly soluble in water.

I claim:

1. An iodine labelled compound having the intended function of a tracer for use in radioimmunology as a labeled antigen, wherein said compound is constituted by a conjugate compound obtained by condensing an antigen having a free carboxylic function and a dipeptide, said dipeptide being constituted by a product of condensation between tyrosine and glycine, the tyrosine group of said dipeptide being labeled with radioactive iodine.

2. A compound according to claim 1, wherein the antigen is constituted by the juvenile hormone.

3. A compound according to claim 1, wherein the antigen is constituted by a prostaglandin.

4. A compound according to claim 1, wherein the antigen is a succinyl derivative of serotonin.

5. A compound according to claim 1, wherein the antigen is abscissic acid.

6. A compound according to claim 1, wherein the antigen is progesterone.

7. A compound according to claim 1, wherein the iodine compound is an analog iodinated derivative of serotonin constituted by a conjugate compound of 5-hydroxy-indole acetic acid and of the glycyl-tyrosine dipeptide, the tyrosine group being labeled with radioactive iodine.

8. A method of preparing a compound according to claim 1, which method comprises condensing an antigen with a dipeptide condensation product of tyrosine and glycine, and thereafter iodinating, the tyrosine group with radioactive iodine.

9. A method according to claim 8, wherein the antigen is previously activated by ethyl chloroformate.

10. A method of preparing a compound according to claim 1, which method comprises first iodinating with radioactive iodine a dipeptide condensation product of tyrosine and glycine to label the tyrosine group thereof with said iodine, and thereafter condensing the thus iodinated dipeptide with an antigen.

* * * * *